United States Patent [19]

Mizukuchi

[11] 4,138,359

[45] Feb. 6, 1979

[54] LIQUID CRYSTAL COMPOSITION AND METHOD FOR MAKING SAME

[75] Inventor: Yutaka Mizukuchi, Saitama, Japan

[73] Assignee: Citizen Watch Co., Ltd., Tokyo, Japan

[21] Appl. No.: 771,991

[22] Filed: Feb. 25, 1977

[30] Foreign Application Priority Data

May 25, 1976 [JP] Japan .................................. 51-59629

[51] Int. Cl.$^2$ .......................... C09K 3/34; G02F 1/13; C07C 69/78; C07C 79/46; C07C 69/62
[52] U.S. Cl. ............................... 252/299; 260/465 D; 350/350; 560/20; 560/73; 560/107
[58] Field of Search ................ 252/299; 350/160 LC, 350/350; 260/465 D, 471 R, 473 R; 560/20, 73, 107

[56] References Cited

U.S. PATENT DOCUMENTS

| | | | |
|---|---|---|---|
| 3,772,389 | 11/1973 | Lowrance, Jr. | 260/465 D |
| 3,925,238 | 12/1975 | Gavrilovic | 252/299 |
| 3,947,375 | 3/1976 | Gray et al. | 252/299 |
| 3,951,846 | 4/1976 | Gavrilovic | 252/299 |
| 3,952,046 | 4/1976 | Scherrer et al. | 260/463 |
| 3,953,491 | 4/1976 | Steinstrasser et al. | 252/299 |
| 3,971,824 | 7/1976 | Van Meter et al. | 260/473 R |
| 4,017,416 | 4/1977 | Inukai et al. | 252/299 |
| 4,029,594 | 6/1977 | Gavrilovic | 252/299 |
| 4,035,056 | 7/1977 | Coates et al. | 252/299 |
| 4,065,489 | 12/1977 | Steinstrasser et al. | 252/299 |
| 4,073,742 | 2/1978 | Erdmann et al. | 252/299 |

FOREIGN PATENT DOCUMENTS

| | | | |
|---|---|---|---|
| 2348193 | 4/1974 | Fed. Rep. of Germany | 252/299 |
| 2600558 | 7/1976 | Fed. Rep. of Germany | 252/299 |
| 4995880 | 9/1974 | Japan | 252/299 |

OTHER PUBLICATIONS

Liquid Crystals & Plastic Crystals, vol. 1, Gray, G. W. et al., John Wiley & Sons, Inc., N.Y., pp. 103-152 (1974).

*Primary Examiner*—Benjamin R. Padgett
*Assistant Examiner*—T. S. Gron
*Attorney, Agent, or Firm*—Koda and Androlia

[57] ABSTRACT

A new and novel liquid crystal composition having broad temperature and chemical stability is disclosed. The liquid crystal composition comprises a compound having the general formula:

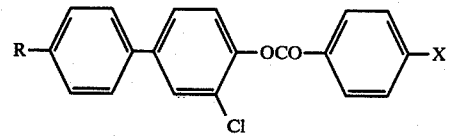

wherein R represents an alkyl or alkoxyl group and X represents an alkyl, alkoxyl, nitro or cyano group. The method for making the liquid crystal compound includes the methylation of 4-phenyl-2-chlorophenol and like compounds.

5 Claims, No Drawings

LIQUID CRYSTAL COMPOSITION AND METHOD FOR MAKING SAME

BACKGROUND OF THE INVENTION

1. Field of the Invention

This invention relates to liquid crystal compositions which include a specific biphenyl-like liquid crystal material and the method for making the same.

2. Prior Art

The use of liquid crystal materials in timepieces and the like is well-known in the art. Displays including these liquid crystal materials are often referred to as liquid-crystal displays (LDCs) which are not self illuminating; they simply absorb or scatter ambient light and thus operate either in the reflective or transmissive mode. The LCD is turned on and made visible by a voltage-controlled change in the refractive index of the display medium. Nematic liquid-crystals presently dominate liquid-crystal display technology. The word "nematic" is derived from the Greek word for thread and refers to microscopic thread-like boundaries separating the LC medium's various domains of molecular orientation. The term "liquid crystal" refers to the nature of the display medium; it is organic, and pours, flows and otherwise behaves as a normal liquid, yet its cigar-shaped molecules have a orderliness that makes the fluid behave optically like a crystal.

Apart from the nematic, the cholesteric type of liquid crystals is one of the few other LC phases of current interest in display technology. Cholesteric liquid crystals change color under the influence of temperature and pressure, for example, but mixtures of these liquid crystals have had problems in terms of their storage stability properties. In a typical display device, the basic display consists of a thin layer of LC solution sandwiched between two thin glass plates. A transparent electrode material, usually tin oxide, forms a 7-segment numeral on the inside surface of the front plate, as well as a non-segmented electrode pattern on the inside surface of the rear plate. In reflective structures, a highly-reflective electrode material, such as chromium, aluminum or nickel, which serves as a mirror, is deposited on the rear plate.

In its quiescent state, the LC medium is transparent, (i.e., the display is dark) because of the orderly array of its cigar-shape molecules. When a voltage is applied between the electrodes, an electric field is created that disorders the LC molecules, thus rendering the medium opaque in the vicinity of the field, scattering the light. The segmented electrodes selectively activate the medium; activated areas appear brighter than the unactivated areas, and a numeral appears. This type of operation is generally referred to in the art as dynamic scattering. Because light is scattered away (in the same direction as that of the incident light), the dynamic scattering operation requires a reflector when the observer's eye is in front of the LC cell, as in a watch display. Direct-current operation shortens life, therefore, such displays use an AC drive signal.

Field-effect LCD's transmit polarized light in their quiescent state and block it in the presence of an electric field. Current flow is not necessary, as in the dynamic-scattering mode. In a field-effect LCD, the preferred alignment of molecules near one glass plate is at 90° to the alignment near the other plate. In effect, the LC molecule alignment is twisted through 90° across thickness of the cell. Thus, field-effect operation is also referred to as twisted-nematic operation.

Although the basic cell structure is the same as that of the dynamic-scattering cell, polarizer elements are added, crossed at 90°, at the front and rear plates. Polarized light enters the unactivated cell, is rotated 90° by the molecular twist of the LC medium, and thus exits the cell through the cross-polarizer at the rear. When activated by an electric field, the molecular alignment "straightens-out" and passes the polarized incident light directly to the rear cross-polarizer without further rotation. The rear polarizer now blocks the light, and an observer behind the cell sees a dark display on a light background. Angularly aligning the polarizers creates a light display on a dark background. Placing a mirror behind the second polarizer creates a reflective cell.

Reflective field effect LCD's provide a significantly higher contrast ratio and thus are generally easier to read than reflective dynamic-scattering devices. It is also possible to generate color in field effect displays; however, the same problem is present, namely, the use of the liquid crystal material therein to create such color and light scattering is not thermally or chemically stable.

Thus, the above-identified problems are of significant proportions given the fact that chemical contamination, including impurities from the glass, and discoloration, can render the entire display device useless. Shortened lifetimes and poor performance result from contaminated LC material and are further enhanced because the rate of decomposition is accelerated when the device is turned on.

Examples of electrochromatic displays are disclosed in U.S. Pat. Nos. 3,839,857 and 3,652,149.

When one traces the history of the materials used in such display elements, a variety of liquid crystal materials have been developed and introduced. Among these materials used include biphenyl liquid crystals and ester liquid crystals. These types of liquid crystals have been used because of their relatively good colorlessness and chemical stability. However, these prior art materials, by themselves, have a rather narrow temperature stability range and therefore are generally used as a mixed composition with other more temperature stable materials. For example, the operating temperature range of typical biphenyl liquid crystal materials are as follows:

| | Liquid Crystal Operating Temperature Range |
|---|---|
| $C_5H_{11}$—⟨⟩—⟨⟩—CN | 22 – 35° C |
| $C_6H_{13}$—⟨⟩—⟨⟩—CN | 58 – 76° C |
| Equal mixture by mole of (1) and (2) | 10°–55° C |
| $C_7H_{15}$—⟨⟩—COO—⟨⟩—CN | – 42° C |
| $C_5H_{11}O$—⟨⟩—OCO—⟨⟩—$OCO_2C_5H_{11}$ | 45 – 72° C |

-continued

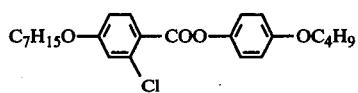
45 – 70° C

As described above, these conventional biphenyl and ester liquid crystal materials have a generally narrow temperature range for displaying purposes. The lowest point of the temperature range indicates the transient temperature from solid state to nematic state and the highest point indicates the transient temperature from nematic state to isotropic state.

The purpose of this invention is to provide a liquid crystal material which has excellent chemical stability, at least as good as the biphenyl liquid crystal materials and ester liquid crystal materials and, in addition, has a broad range of temperature stability. In order to achieve this object, biphenyl benzoyl ester having lateral chlorine substitution is derived.

The novel features which are believed to be characteristic of the invention, both in its organization and method of operation, together with further objectives and advantages thereof, will be better understood from the following description in which presently preferred embodiments of the invention are illustrated by way of examples. It is to be expressly understood, however, that the examples are for the purpose of illustration and description only and are not intended as a definition of the limits of the invention.

DESCRIPTION OF THE PREFERRED EMBODIMENTS

The typical liquid crystal materials of the present invention and their operating temperature range are as follows:

| | General Formula | Liquid Crystal Temperature Range |
|---|---|---|
| Compound 1 | 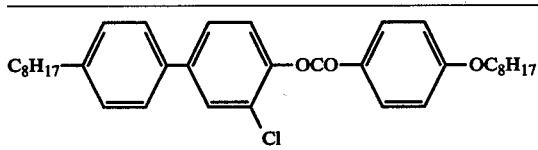 | 55 – 115° C |
| Compound 2 | 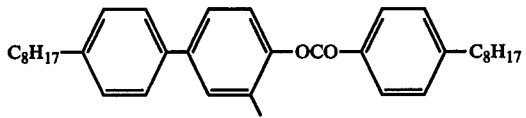 | 36 – 86° C |
| Compound 3 | 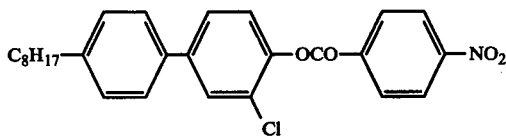 | 74 – 104° C |

The methods for making the compounds of the present invention and examples of liquid crystal compositions comprising these compounds are described hereinbelow.

EXAMPLE 1

4-phenyl-2-chlorophenol is methylated by means of well-known method steps and 4-phenyl-2-chloroanisole (hereinafter referred to as Material I) is extracted. $\frac{1}{3}$ mole of Material I is dissolved into carbon disulfide 300cc and a Friedel Craft's reaction is effected in a MILO flask in which $\frac{1}{3}$ mole of octanol chloride and 60 grams of anhydrous ammonium chloride are placed. As a result, 4-octanoyl-4'-methoxy-3'-chlorobiphenyl (hereinafter referred to as Compound 4) is extracted with a yield of 75%. As the result of reduction of said Compound 4, by the well-known Wolff-Kischner's reaction, 4-octyl-4'-methoxy-3'-chlorobiphenyl (hereinafter referred to as Compound 5) is extracted with a yield of 70 weight percent. 0.01 mole of 4-octyl-4'-hydroxy-3-chlorobiphenyl (hereinafter referred to as Material II), which is extracted from said Compound 5 by means of demethylation with HBr water, is dissolved into a mixed solution of 100cc pyridine and 50cc. of benzene. After this 0.012 mole of 4-octyloxy-benzoil chloride is added to the solution, this mixed solution is heated and stirred for 24 hours. Extraction is achieved by adding water (200cc) and benzene (100cc) to the solution. The resultant benzene layer is washed with a mixture of 1 mole of sodium hydroxide solution (50cc) and 1 mole of HCl liquid (100cc). The resultant compound in benzene layer is crystallized from ethyl alcohol (50cc). The result of the above method steps, 4-octyl-4'-(4"-octyloxy benzoil)-3'-chlorobiphenyl (Compound 1 in the above table), is extracted at the yield rate of 85%.

EXAMPLE 2

0.01 mole of said Material II is dissolved into 30cc of alcohol to which are added 0.6 grams of KOH into the solution. After these steps, potassium salt of Material II is isolated by removing the alcohol and is dispersed in 50cc of chloroform. 0.01 mole of 4-nitro benzoil chloride is added into the solution and heated and stirred for an hour. Next the following three method steps are performed. First, benzene (100cc) is added into the reaction solution. The benzene is washed with a mixture of 200cc of water and 1 mole of sodium hydroxide solution (200cc). The resultant mixture is distilled, driving off the benzene and the chloroform which is a solvent in the previous step. Finally, recrystallization from the alcohol takes place whereby said Compound 3 in the above table is extracted at the yield rate of 85 weight percent.

For example equal mixtures by mole of said Compound 1 and said Compound 2 form a liquid crystal composition which has a liquid crystal temperature range of 5°–100° C. and is extremely chemically-stable.

As described hereinabove, the compounds of the present invention are liquid crystal materials which have a broad liquid crystal temperature range by themselves or when mixed with each other. The chemical stability has been found to be even better than the biphenyl liquid crystals and ester liquid crystals, thus lending the compounds of the present invention to their use as liquid crystals for display elements, such as watches and the like, and to the use of such LCD in mixtures with biphenyls and ester-based liquid crystals.

What is claimed is:

1. A liquid crystal compound having the formula:

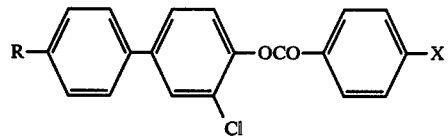

wherein R represents an alkyl group of eight carbon atoms and X represents an alkyl group of eight carbon atoms, alkoxyl group of eight carbon atoms or a nitro group.

2. The compound according to claim 1, wherein X is alkyl of eight carbon atoms.

3. The compound according to claim 1, wherein X is alkoxyl of eight carbon atoms.

4. The compound according to claim 1, wherein X is $NO_2$.

5. A liquid crystal composition comprising a mixture of at least two different compounds as defined in claim 1.